United States Patent
Tian et al.

(10) Patent No.: US 12,350,304 B2
(45) Date of Patent: Jul. 8, 2025

(54) RECOMBINANT ONCOLYTIC VIRUS COMPOSITION AND USE THEREOF

(71) Applicant: BEIJING WELLGENE COMPANY LTD., Beijing (CN)

(72) Inventors: Chao Tian, Beijing (CN); Xiaopeng Li, Beijing (CN); Chunyang Sun, Beijing (CN); Hua Zhou, Beijing (CN); Jiajia Liu, Beijing (CN); Jingshu Zhao, Beijing (CN)

(73) Assignee: BEIJING WELLGENE COMPANY LTD., Beijing (CN)

( * ) Notice: Subject to any disclaimer, the term of this patent is extended or adjusted under 35 U.S.C. 154(b) by 949 days.

(21) Appl. No.: 17/044,074

(22) PCT Filed: Mar. 21, 2019

(86) PCT No.: PCT/CN2019/078999
§ 371 (c)(1),
(2) Date: Sep. 30, 2020

(87) PCT Pub. No.: WO2019/196617
PCT Pub. Date: Oct. 17, 2019

(65) Prior Publication Data
US 2021/0138008 A1    May 13, 2021

(30) Foreign Application Priority Data
Apr. 13, 2018 (CN) .......................... 201810331305.9

(51) Int. Cl.
| | | |
|---|---|---|
| *A61K 35/763* | (2015.01) |
| *A61P 35/00* | (2006.01) |
| *C07K 14/535* | (2006.01) |
| *C07K 14/54* | (2006.01) |
| *C07K 14/55* | (2006.01) |
| *C07K 16/28* | (2006.01) |
| *C12N 7/00* | (2006.01) |

(52) U.S. Cl.
CPC ............ *A61K 35/763* (2013.01); *A61P 35/00* (2018.01); *C07K 14/535* (2013.01); *C07K 14/5434* (2013.01); *C07K 14/55* (2013.01); *C07K 16/2818* (2013.01); *C12N 7/00* (2013.01); *C12N 2710/16632* (2013.01); *C12N 2710/16643* (2013.01)

(58) Field of Classification Search
CPC .... A61K 35/763; A61K 39/12; A61K 39/245; A61K 39/25; A61K 2039/5254; A61K 35/768; C12N 2710/16034; C12N 2710/16621; C12N 2710/16632; C12N 2710/16622; C12N 2710/16633; C12N 2710/16721; C12N 2710/16722; C12N 15/86; C12N 15/869; C12N 2710/10032; C12N 15/8695; A61P 35/00; A61P 9/10; A61P 31/20; A61P 35/04; C07K 14/535; C07K 14/5434

See application file for complete search history.

(56) References Cited

U.S. PATENT DOCUMENTS

| | | | |
|---|---|---|---|
| 10,570,377 B2 * | 2/2020 | Coffin ................ | C07K 16/2818 |
| 2015/0202290 A1 | 7/2015 | Vanderwalde et al. | |

FOREIGN PATENT DOCUMENTS

| | | |
|---|---|---|
| CN | 103055325 A | 4/2013 |
| CN | 104704002 A | 6/2015 |
| CN | 106999577 A | 8/2017 |
| CN | 108635380 A | 10/2018 |
| WO | 9907394 A1 | 2/1999 |
| WO | 2016009017 A1 | 1/2016 |
| WO | 2017118866 A1 | 7/2017 |
| WO | 2018064134 A1 | 4/2018 |
| WO | 2019196617 A1 | 10/2019 |

OTHER PUBLICATIONS

De Graaf J F et al., "Armed oncolytic viruses: A kick-start for anti-tumor immunity," Cytokine & Growth Factor Reviews, vol. 41:28-39 (2018).

Extended European Search Report, EP Application No. 19784788.2, dated Apr. 29, 2021, 11 pages.

Ino Y. et al., "Triple combination of oncolytic herpes simplex virus-1 vectors armed with interleukin-12, interleukin-18, or soluble B7-1 results in enhanced anti-tumor efficacy", Clinical Cancer Research, American Association for Cancer Research, US, vol. 12(2): 643-652 (2006).

Parker, J.N. et al., "Enhanced inhibition of syngeneic murine tumors by combinatorial therapy with genetically engineered HSV-1 expressing CCL2 and IL-12", Cancer Gene Therapy, vol. 12(4):359-368(2005).

Zhang W. et al., "Combination of Oncolytic Herpes Simplex Viruses Armed with Angiostatin and IL-12 Enhances Antitumor Efficacy in Human Glioblastoma Models", Neoplasia, vol. 15(6):591-599(2013).

Feng Chao, "The Preliminary Study of the Effect of Oncolytic Viruse Armed with IL-33 or IL-36 gamma on Synergistically Inhibiting Tumor Effect", CNKI Master's Theses Full-text Database, 68 pages (2016).

(Continued)

*Primary Examiner* — Bao Q Li
(74) *Attorney, Agent, or Firm* — Nelson Mullins Riley & Scarborough LLP; Jill Gorny Sloper, Esq.

(57) ABSTRACT

Provided is a recombinant oncolytic virus composition, comprising a first recombinant oncolytic virus and a second recombinant oncolytic virus. Both the first and second recombinant oncolytic viruses comprise a herpes simplex virus vector and an exogenous gene, the exogenous gene is encoded from one of cytokine, a monoclonal antibody having a tumor preventative and/or treatment function, tumor antigens, prodrug invertase, tumor suppressor polypeptide, antisense RNA or small RNA, wherein the exogenous genes in the first and the second recombinant oncolytic viruses are different. Also provided is an application of the recombinant oncolytic virus composition in preparation of a medicament drug for treating tumors.

11 Claims, No Drawings

(56) References Cited

OTHER PUBLICATIONS

Gao Kai, et al., "Quality Control Research on Recombinant Oncolytic Herpes Simplex Virus Serotype 1 Encoding Human GM-CSF Gene", Chin Pharm J., Nov. 31, 2011, vol. 46 No. 19, p. 1520-1525.
International Preliminary Report on Patentability, PCT/CN2019/078999, dated Oct. 13, 2020, 14 pages.
International Search Report and Written Opinion, PCT/CN2019/078999, dated May 17, 2019, 24 pages.
Liu Pengying, "Research Progress in the Application of Cytokine Induced Killer Cells to Cancer Adoptive Immunotherapy," Journal of Medical Postgraduates, vol. 21(8): 885-889 (2008).

* cited by examiner

RECOMBINANT ONCOLYTIC VIRUS COMPOSITION AND USE THEREOF

RELATED INFORMATION PARAGRAPH

This application is a 35 U.S.C. 371 national stage filing of International Application No. PCT/CN2019/078999, filed on Mar. 21, 2019, which claims the benefit of the priority date of Chinese Application No. CN201810331305.9, filed on Apr. 13, 2018, the content of which is hereby incorporated by reference in its entirety.

FIELD OF THE INVENTION

The present invention relates to the field of genetic engineering, in particular to a recombinant oncolytic virus composition and the use thereof in the preparation of a medicament for treating tumor.

BACKGROUND OF THE INVENTION

1. Application of Oncolytic Virus in Tumor Treatment

Traditional tumor treatment includes surgery, radiotherapy and chemotherapy, with low treatment efficiency and high recurrence rate. Tumor gene immunotherapy is a rapidly progressing anti-tumor method in recent years with great potential. Among the top 10 scientific breakthroughs in 2013 selected by the "Science" journal, tumor immunotherapy topped the list. Among them, the oncolytic virus represented by the HSV-1 vector has played a huge role in tumor immunotherapy.

Oncolytic virus refers to a type of virus that can selectively infect a tumor cell and replicate in a target cell, ultimately leading to tumor cell lysis and death. This type of virus relies on its own specificity to replicate in a tumor cell to lyse the tumor cell. The virus released after cell lysis can further infect surrounding tumor cells, and at the same time has no damage or little effect to normal cells and tissues. Oncolytic virus has multiple anti-tumor mechanisms, including: 1. directly lysing a tumor cell; 2. destroying a tumor blood vessel; 3. a viral protein expressed in virus replication having direct cytotoxic effect; 4. an anti-tumor immune response; 5. enhancing sensitivity of a tumor cell to radiotherapy and chemotherapy; 6. expression of the inserted exogenous therapeutic gene. The virus currently used for oncolytic virus engineering includes herpes simplex virus, adenovirus, and vaccinia virus, in which herpes simplex virus type I (HSV-1) is the most promising virus vector.

HSV-1 is a large double-stranded DNA virus with a genome size of 152 kb and encodes more than 80 genes. Among them, the γ34.5 gene product can block the synthesis of host protein caused by virus infection, while the deletion of γ34.5 makes a virus vector unable to replicate in normal cells, and at the same time the γ34.5 gene product is a neurotoxic factor. The ICP6 gene in HSV-1 encodes and expresses the large subunit of the viral ribonucleotide reductase, which is an enzyme necessary for HSV-1 in the synthesis of viral DNA in a non-dividing cell. Thymidine kinase expressed by the TK gene participates in the synthesis of phosphorylated deoxynucleosides, and at the same time phosphorylates deoxycytidine and a nucleoside analog, producing a viral DNA synthesis precursor. UNG gene expresses uracil glycosylase which can excise uracil from DNA to prevent mutations and signal the base splicing repair pathway. ICP47 gene product blocks antigen presentation during virus infection (Shen Y, Nemunaitis J. Herpes simplex virus 1(HSV-1) for cancer treatment. Cancer Gene Therapy 2006; 13:975-992 ; Peters C, Rabkin S D. Designing Herpes Viruses as Oncolytics. Molecular Therapy Oncolytics, 2015, 2:15010).

2. Oncolytic Virus Combination Therapy

A tumor cell has a variety of immune escape mechanisms, and no single treatment strategy can completely eliminate the tumor cell. Therefore, the combined application of multiple treatment strategies will be the development trend of tumor treatment in the future.

The combination therapy with oncolytic virus and other treatment methods or drugs usually adopt two strategies. One is that the oncolytic virus and other treatment methods or drugs are administered separately in a unified treatment protocol. The other is that oncolytic virus carries a gene that is beneficial to tumor treatment.

However, none of the existing treatment methods can kill tumor continuously and efficiently.

SUMMARY OF THE INVENTION

The purpose of the present invention is to overcome the aforementioned problem in the prior art. Provided is a recombinant oncolytic virus composition, which can retain the highly efficient tumor killing effect of the oncolytic virus, at the same time by adjusting the amount of each component of the recombinant oncolytic virus composition, maximize the synergistic anti-tumor effect of the exogenous genes expressed by each component and of the expressed exogenous genes and the oncolytic virus, and reduce the side effects of treatment.

Specifically, the present invention relates to:

1. A recombinant oncolytic virus composition, characterized in that the composition contains:
   a first recombinant oncolytic virus, comprising a first herpes simplex virus vector and a first exogenous gene; the first exogenous gene is a gene encoding any one of the following: cytokine, a monoclonal antibody having preventative and/or therapeutic effect on tumor, a tumor antigen, prodrug invertase, a tumor suppressor protein, antisense RNA or small RNA that blocks or down-regulates overexpressed proto-oncogene and a metabolic gene in tumor;
   a second recombinant oncolytic virus, comprising a second herpes simplex virus vector and a second exogenous gene; the second exogenous gene is a gene encoding any one of the following: cytokine, a monoclonal antibody having preventative and/or therapeutic effect on tumor, a tumor antigen, prodrug invertase, a tumor suppressor protein, antisense RNA or small RNA that blocks or down-regulates overexpressed proto-oncogene and a metabolic gene in tumor;
   wherein, the first herpes simplex virus vector and the second herpes simplex virus vector are the same or different from each other, and the selected first exogenous gene is different from the selected second exogenous gene.
2. The recombinant oncolytic virus composition according to item 1, wherein the composition further contains a third recombinant oncolytic virus, and the third recombinant oncolytic virus includes a third herpes simplex virus vector and a third exogenous gene; the third exogenous gene is a gene encoding any one of the following: cytokine, a monoclonal antibody having preventative and/or therapeutic effect on tumor, a tumor antigen, prodrug invertase, a tumor suppressor protein, antisense RNA or small RNA that blocks or down-regulates overexpressed proto-oncogene and a metabolic gene in tumor;

wherein, the third herpes simplex virus vector and the first herpes simplex virus vector are the same or different, and the selected third exogenous gene is different from the selected first exogenous gene; and, the third herpes simplex virus vector and the second herpes simplex virus vector are the same or different, and the selected third exogenous gene is different from the selected second exogenous gene.

3. The recombinant oncolytic virus composition of claim 1 or 2, wherein the cytokine is any one selected from the group consisting of: GM-CSF, G-CSF, M-CSF, IL-1, IL-2, IL-3, IL-4, IL-5, IL-6, IL7, IL-8, IL-10, IL-12, IL-13, IL-15, IL-18, IL-21, IL-23, IFN-α, IFN-γ, TGF-β and TNF-α.

4. The recombinant oncolytic virus composition according to item 1 or 2, wherein the monoclonal antibody having preventative and/or therapeutic effect on tumor is any one selected from the group consisting of: PD-1 monoclonal antibody, PD-L1 monoclonal antibody, PD-L2 monoclonal antibody, CTLA-4 monoclonal antibody, CD80 monoclonal antibody, CD28 monoclonal antibody, CD137 monoclonal antibody, CD137L monoclonal antibody, OX40 monoclonal antibody, OX40L monoclonal antibody, CD27 monoclonal antibody, CD70 monoclonal antibody, CD40 monoclonal antibody, CD40L monoclonal antibody, LAG-3 monoclonal antibody and TIM-3 monoclonal antibody.

5. The recombinant oncolytic virus composition of item 1 or 2, wherein the tumor antigen is a tumor-specific antigen or a tumor-associated antigen.

6. The recombinant oncolytic virus composition of item 5, wherein the tumor antigen is any one selected from the group consisting of: PSA, MUC1, MAGE-1, MAGE-2, MAGE-3, MAGE-12, BAGE, GAGE and LAGE.

7. The recombinant oncolytic virus composition according to any one of items 1-6, wherein the first exogenous gene, the second exogenous gene, and the third exogenous gene each independently comprise an expression control sequence operably linked to it, the expression control sequence includes at least one of a promoter, an enhancer and a polynucleotide.

8. The recombinant oncolytic virus composition according to any one of items 1-7, wherein the first herpes simplex virus vector, the second herpes simplex virus vector, and the third herpes simplex virus vector are each independently herpes simplex virus with the deletion of the gene encoding ICP34.5, or herpes simplex virus with the deletion of the genes encoding ICP34.5 and ICP47, and the first herpes simplex virus vector, the second herpes simplex virus vector and/or the third herpes simplex virus vector are the same or different from each other.

9. The recombinant oncolytic virus composition according to item 8, wherein the first herpes simplex virus vector, the second herpes simplex virus vector, and the third herpes simplex virus vector are further with the deletion of at least one of the genes encoding ICP6, TK and UNG.

10. The recombinant oncolytic virus composition according to any one of items 1-9, wherein the insertion site of the exogenous gene is any one of the positions on the herpes simplex virus vector where the coding gene is deleted, and the insertion sites of the first exogenous gene, the second exogenous gene and/or the third exogenous gene are the same or different from each other.

11. The recombinant oncolytic virus composition according to item 10, wherein the insertion site of the first exogenous gene, the second exogenous gene and/or the third exogenous gene is a position where the gene encoding ICP34.5 is deleted.

12. The recombinant oncolytic virus composition according to any one of 1-11, wherein the herpes simplex virus is herpes simplex virus type 1 (HSV-1).

13. The recombinant oncolytic virus composition according to any one of items 1-12, wherein the first exogenous gene is a gene encoding a cytokine, and the second exogenous gene is a gene encoding a monoclonal antibody.

14. The recombinant oncolytic virus composition according to item 13, wherein the first exogenous gene is a gene encoding GM-CSF, G-CSF, M-CSF, IL-2, IL-12 or IFN-γ, and the second exogenous gene is a gene encoding an immune checkpoint blocking antibody.

15. The recombinant oncolytic virus composition according to item 14, wherein the first exogenous gene is a gene encoding GM-CSF, IL-2 or IL-12, and the second exogenous gene is a gene encoding PD-1 blocking monoclonal antibody, PD-L1 blocking monoclonal antibody.

16. The recombinant oncolytic virus composition according to any one of items 11-15, wherein, in terms of pfu, the mixing ratio of the first recombinant oncolytic virus to the second recombinant oncolytic virus is 0.5:8, 1:8, 1:7, 1:6, 1:5, 1:4, 1:3, 1:2, 1:1.

17. The recombinant oncolytic virus composition according to any one of items 1-11, wherein the first exogenous gene and the second exogenous gene are a gene encoding cytokine, and the first exogenous gene and the second exogenous gene encode different cytokines.

18. The recombinant oncolytic virus composition of item 17, wherein the cytokine is selected from: GM-CSF, G-CSF, M-CSF, IL-2, IL-12 and IFN-γ.

19. The recombinant oncolytic virus composition of item 18, wherein the cytokine is selected from: GM-CSF, IL-2 and IL-12.

20. The recombinant oncolytic virus composition according to any one of items 17-19, wherein, in terms of pfu, the mixing ratio of the first recombinant oncolytic virus to the second recombinant oncolytic virus is 0.5:2 to 2:0.5, preferably 0.5:1 to 1:0.5, most preferably 1:1.

21. Use of the recombinant oncolytic virus composition according to any one of items 1-20 in the preparation of a medicament for treating tumor.

22. The use according to item 21, wherein the tumor is selected from at least one of brain glioma, melanoma, liver cancer, lung cancer, colorectal cancer, head and neck cancer, breast cancer, renal cell carcinoma, ovarian cancer, prostate cancer, gastric cancer, lymphoma, pancreatic cancer, bladder cancer, breast cancer, endometrial cancer, lymphoma, and sarcoma (e.g., soft tissue sarcoma and osteosarcoma).

23. A pharmaceutical composition, comprising the recombinant oncolytic virus composition according to any one of items 1-20 and a pharmaceutically acceptable carrier.

24. A product or kit, comprising a vial containing the pharmaceutical composition of item 23 and a package insert recording information related to the use of the pharmaceutical composition.

25. A method for treating tumor, comprising administering to a subject an effective amount of the recombinant oncolytic virus composition of any one of items 1-20 or the pharmaceutical composition of item 23.

26. The method according to claim 25, wherein the tumor is selected from at least one of brain glioma, melanoma, liver cancer, lung cancer, colorectal cancer, head and neck cancer, breast cancer, renal cell carcinoma, ovarian cancer, prostate cancer, gastric cancer, lymphoma, pancreatic cancer, bladder cancer, breast cancer, endometrial cancer, lymphoma, and sarcoma (e.g., soft tissue sarcoma and osteosarcoma).

DETAIL DESCRIPTION OF THE INVENTION

1. Definitions

"Oncolytic virus" refers to a type of virus that infects and kills cancer cells. After infecting cancer cells, the virus destroys the infected cancer cells through oncolytic effect, and at the same time releases new infectious virus particles or virions, destroying the remaining cancer cells. This type of virus gets its name from its oncolytic effect.

As "Herpes Simplex Virus (HSV)" is easy to handle and relatively harmless in its natural state, it's one of the first viruses (oncolytic viruses) chosen to selectively attack cancer cells. The herpes simplex virus type 1 (HSV-1) mutant 1716 lacks two copies of the ICP34.5 gene, so it can no longer replicate in terminally differentiated and non-dividing cells, but can infect cancer cells and cause cancer cell lysis in a very effective way, which has been proven to be an effective tumor targeting strategy. A variety of HSV-based oncolytic viruses have been developed and are undergoing clinical trials.

When the virus of the present invention is herpes simplex virus, the virus can be derived from, for example, HSV1 strain or HSV2 strain or their derivative strains, preferably HSV1. Derivative strains include inter-type recombinants containing DNA from HSV1 strain and HSV2 strain. The sequence homology between the derivative strain and HSV1 genome or HSV2 genome is preferably at least 70%, more preferably at least 80%, even more preferably at least 90% or 95%. More preferably, the sequence identity of the derivative strain with the HSV1 genome or HSV2 genome is at least 70%, more preferably at least 80%, even more preferably at least 90%, 95% or 98% identity.

"Herpes simplex virus vector" refers to herpes simplex virus that carries an exogenous gene.

Plaque forming unit, abbreviated pfu, refers to the number of viruses that form a plaque (barren spot) on a monolayer of cultured animal cells.

"Immune checkpoint blocking (inhibitory) antibody" or "immune checkpoint blocking (inhibitory) monoclonal antibody" refer to a monoclonal antibody that inhibits or blocks an inhibitory immune checkpoint molecule. Immune checkpoint is a regulator of the immune system. Their role is to prevent the immune system from attacking cells indiscriminately, which is crucial for self tolerance. Immune checkpoint is divided into an inhibitory checkpoint molecule and a stimulatory checkpoint molecule. The inhibitory checkpoint molecule includes but is not limited to: A2AR, B7-H3 (CD276), B7-H4, BTLA (CD272), CTLA-4 (CD152), IDO, KIR, LAG3, NOX2, PD1, TIM3, VISTA; the stimulatiory checkpoint molecule includes but is not limited to: CD27, CD40, OX40, GITR, CD137, CD28, ICOS. Inhibitory checkpoint molecules are targets for cancer immunotherapy because they may be used in many types of cancer.

The term "synergistic" as used in the present invention means that the oncolytic effect (tumor treatment effect) of the composition containing two or more recombinant oncolytic viruses of the present invention is greater than the oncolytic effect (tumor treatment effect) by using any one of the recombinant oncolytic viruses independently and separately. For example, the relative tumor inhibition rate achieved by administering to a subject a composition comprising two or more recombinant oncolytic viruses of the present invention, comparing to the relative tumor inhibition rate achieved by administering to a subject any one of the recombinant oncolytic viruses in the composition independently, is increased by 50%, 45%, 40%, 35%, 30%, 25%, 20%, 15% or 10%, for example, increased by 10%-50%, 15%-45%, 20%-40%, 25%-35%, 20%-30%, 20%-35%, 20%-45%. The numerical range here covers both the values of the endpoints and any value between the endpoints, as if these values were listed herein one by one. Relative tumor inhibition rate (TGI) (%)=(1−T/C)×100%. T/C% is the relative tumor proliferation rate, i.e., the percentage value of the relative tumor volume of the treatment group to that of the control group at a specific time point. T and C are the relative tumor volume (RTV) of the treatment group and the control group at a specific time point, respectively. RTV=animal tumor volume after treatment/tumor volume in control group. The synergistic effect exhibited by the recombinant oncolytic virus composition of the present invention is based on the comparison of the oncolytic effect (for example, relative tumor inhibition rate) of the composition and the oncolytic effect (for example, relative tumor inhibition rate) of a separate recombinant oncolytic virus, as shown in the examples of this application. The comparison methods used in the examples of this application are also common comparison and determination methods commonly used in the art to prove whether two drugs (or treatment methods) can generate synergistic effects.

2. The Recombinant Oncolytic Virus Composition of the Present Invention

One aspect of the present invention relates to a recombinant oncolytic virus composition, characterized in that the composition contains:

a first recombinant oncolytic virus, the first recombinant oncolytic virus comprising a first herpes simplex virus vector and a first exogenous gene; the first exogenous gene is a polynucleotide sequence encoding any one of the following: cytokine, a monoclonal antibody having preventative and/or therapeutic effect on tumor, a tumor antigen, prodrug invertase, a tumor suppressor protein, antisense RNA or small RNA that blocks or down-regulates overpressed proto-oncogene and a metabolic gene in tumor;

a second recombinant oncolytic virus, the second recombinant oncolytic virus comprising a second herpes simplex virus vector and a second exogenous gene; the second exogenous gene is a gene encoding any one of the following: cytokine, a monoclonal antibody having preventative and/or therapeutic effect on tumor, a tumor antigen, prodrug invertase, a tumor suppressor protein, antisense RNA or small RNA that blocks or down-regulates overpressed proto-oncogenes and a metabolic gene in tumor;

wherein, the first herpes simplex virus vector and the second herpes simplex virus vector are the same or different from each other, and the selected first exogenous gene is different from the selected second exogenous gene.

In some embodiments, the aforementioned recombinant oncolytic virus composition of the present invention further contains another one or more recombinant oncolytic viruses. For example, the aforementioned recombinant oncolytic virus composition of the present invention further contains a third recombinant oncolytic virus, the third recombinant oncolytic virus including a third herpes simplex virus vector and a third exogenous gene; the third exogenous gene is a gene coding any one selected from the following: cytokine, a monoclonal antibody having preventative and/or therapeutic effect on tumor, a tumor antigen, prodrug invertase, a tumor suppressor proteins, antisense RNA or small RNA that blocks or down-regulates overpressed proto-oncogene and a metabolic gene in tumor;

wherein, the third herpes simplex virus vector and the first herpes simplex virus vector are the same or different, and the selected third exogenous gene is different from the selected first exogenous gene; and, the third herpes simplex virus vector and the second herpes simplex virus vector are the same or different, and the selected third exogenous gene is different from the selected second exogenous gene.

In some embodiments, in the aforementioned recombinant oncolytic virus composition of the present invention, the cytokine is any one selected from the group consisting of: GM-CSF, G-CSF, M-CSF, IL-1, IL-2, IL-3, IL-4, IL-5, IL-6, IL7, IL-8, IL-10, IL-12, IL-13, IL-15, IL-18, IL-21, IL-23, IFN-α, IFN-γ, TGF-β and TNF-α. In some embodiments, in the aforementioned recombinant oncolytic virus composition of the present invention, the monoclonal antibody having preventative and/or therapeutic effect on tumor is any one selected from the group consisting of: PD-1 monoclonal antibody, PD-L1 monoclonal antibody, PD-L2 monoclonal antibody, CTLA-4 monoclonal antibody, CD80 monoclonal antibody, CD28 monoclonal antibody, CD137 monoclonal antibody, CD137L monoclonal antibody, OX40 monoclonal antibody, OX40L monoclonal antibody, CD27 monoclonal antibody, CD70 monoclonal antibody, CD40 monoclonal antibody, CD40L monoclonal antibody, LAG-3 monoclonal antibody and TIM-3 monoclonal antibody.

In some embodiments, in the aforementioned recombinant oncolytic virus composition of the present invention, the tumor antigen is a tumor-specific antigen or a tumor-associated antigen. In some embodiments, in the aforementioned recombinant oncolytic virus composition of the present invention, the tumor antigen is any one selected from the group consisting of: PSA, MUC1, MAGE-1, MAGE-2, MAGE-3, MAGE-12, BAGE, GAGE and LAGE.

In some embodiments, in the aforementioned recombinant oncolytic virus composition of the present invention, the first exogenous gene, the second exogenous gene, and the third exogenous gene each independently comprise an expression control sequence operably linked to it.

According to the present invention, in order to be able to express the exogenous gene inserted into the herpes simplex virus vector, the first exogenous gene and the second exogenous gene of the present invention preferably each independently include one or more of a promoter, an enhancer, and a polynucleotide (including the terminator sequence). In a preferable case, when infecting host cells and expressing its own genes, the recombinant herpes simplex virus can transcribe and express protein molecules or antisense RNAs or small RNA molecules corresponding to the exogenous genes. Wherein, the promoter may be a promoter known in the art, such as at least one of SV40 promoter, CMV promoter, MSV promoter, EF1 promoter, MMLV promoter, U6 promoter, and H1 promoter; the enhancer may be a promoter known in the art, such as SV40 enhancer and/or CMV enhancer; the terminator may be known in the art, such as SV40 PolyA, TK PolyA and/or BGH PolyA. The types of promoters, enhancers, and polynucleotides included in the first exogenous gene and the second exogenous gene may be the same or different.

Those skilled in the art can understand that, in order to facilitate the expression of exogenous genes, the exogenous genes may also contain other exogenous gene expression control elements in addition to the aforementioned elements, for example, a polyadenylation site, Kozak sequence, WPRE and a downstream enhancer element. These are all known to those skilled in the art, and will not be repeated herein.

In some embodiments, in the aforementioned recombinant oncolytic virus composition of the present invention, the first herpes simplex virus vector, the second herpes simplex virus vector, and the third herpes simplex virus vector are each independently herpes simplex virus with deletion of the gene encoding ICP34.5, or herpes simplex virus with the deletion of the genes encoding ICP34.5 and ICP47, and the first herpes simplex virus vector, the second herpes simplex virus vector, and/or the third herpes simplex virus vector are the same or different from each other.

In some embodiments of the present invention, the first herpes simplex virus vector, the second herpes simplex virus vector, and the third herpes simplex virus vector are further with the deletion of at least one of the genes encoding ICP6, TK and UNG, and, the first herpes simplex virus vector, the second herpes simplex virus vector and/or the third herpes simplex virus vector are the same or different from each other.

In some embodiments, in the aforementioned recombinant oncolytic virus composition of the present invention, the insertion site of the exogenous gene is any one of positions on the herpes simplex virus vector where the encoding gene is deleted, and the insertion sites of the first exogenous gene, the second exogenous gene and/or the third exogenous gene are the same or different from each other. In some embodiments, in the aforementioned recombinant oncolytic virus composition of the present invention, the insertion site of the first exogenous gene, the second exogenous gene and/or the third exogenous gene is a position where the gene encoding ICP34.5 is deleted.

In some embodiments, in the aforementioned recombinant oncolytic virus composition of the present invention, the first exogenous gene is a gene encoding cytokine, and the second exogenous gene is a gene encoding a monoclonal antibody. In some embodiments, in the aforementioned recombinant oncolytic virus composition of the present invention, the first exogenous gene is a gene encoding GM-CSF, G-CSF, M-CSF, IL-2, IL-12 or IFN-γ, the second exogenous gene is a gene encoding an immune checkpoint blocking antibody. In some embodiments, in the aforementioned recombinant oncolytic virus composition of the present invention, the first exogenous gene is a gene encoding GM-CSF, IL-2 or IL-12, and the second exogenous gene is a gene encoding PD-1 blocking monoclonal antibody, PD-L1 blocking monoclonal antibody. The inventors of the present invention found that, in the recombinant oncolytic virus composition, the tumor treatment effects resulted from the selection of exogenous genes are significantly different; and the working concentrations of oncolytic viruses expressing different exogenous genes are also different. For example, for the recombinant oncolytic virus composition of the recombinant oncolytic virus with the insertion of the exogenous gene of cytokine and the recombinant oncolytic virus with the insertion of the exogenous gene of an immune checkpoint blocking antibody, with the increasing concentration ratio of the former and the latter, the oncolytic effect becomes stronger and stronger until the ratio is 1:3 with which the oncolytic effect reaches the highest; and for the recombinant oncolytic virus composition of the recombinant oncolytic virus inserted with the exogenous gene of cytokine, the oncolytic effect in the oncolytic curve reaches strongest when the ratio between the two recombinant oncolytic viruses is 1:1.

Cytokine is a messenger of immune system. In anti-tumor therapy, it can achieve a better tumor killing effect by improving tumor antigen presentation, directly or indirectly activating an immune effector cell and other functions. However, a cytokine pathway generally has gene pleiotropy and redundancy. Many cytokines have dual functions in the process of immune activation and suppression. Moreover, clinical application of high-dose cytokine usually brings a serious side effect. How to obtain a strong anti-tumor effect in the low-toxic dose range is a challenge for cytokine combination therapy. For the recombinant oncolytic virus composition expressing different cytokines and the recombinant oncolytic virus composition expressing cytokines and antibodies herein, not only the different recombinant oncolytic viruses in the composition should be synergistic in the treatment of cancer, but also the inappropriate amount of cytokines causing immune system disorder and producing greater side effect should be avoided. It is necessary to carefully study and adjust the proportion of recombinant oncolytic viruses in the recombinant oncolytic virus composition to achieve the adjustment of the expression of exogenous genes carried by the recombinant oncolytic virus, reducing the side effects caused by the overexpression of exogenous genes or the unbalanced expression of different exogenous genes. Selecting appropriate cytokines and antibodies, or selecting different cytokines, and inserting genes expressing them together into oncolytic virus genome can also have a synergistic effect on tumor killing, as recorded in PCT application PCT/CN2018/091530. However, inserting different exogenous genes together into the oncolytic virus genome cannot achieve the regulation of the expression of different exogenous genes. By mixing the oncolytic viruses each carrying a single exogenous gene in different proportions, not only the regulating of the exogenous gene expression is achieved, but also the best tumor killing effect is carried out, and the side effects are reduced.

In some embodiments, in the recombinant oncolytic virus composition of the present invention, in terms of pfu, the mixing ratio of the first recombinant oncolytic virus to the second recombinant oncolytic virus is about 0.5:8, 1:8, 1:7, 1:6, 1:5, 1:4, 1:3, 1:2, 1:1. In some embodiments, in the aforementioned recombinant oncolytic virus composition of the present invention, the first exogenous gene and the second exogenous gene are genes encoding cytokines, and the cytokines encoded by the first exogenous gene and the second exogenous gene are different. In some embodiments, in the aforementioned recombinant oncolytic virus composition of the present invention, the cytokine is selected from: GM-CSF, G-CSF, M-CSF, IL-2, IL-12 and IFN-γ. In some embodiments, in the aforementioned recombinant oncolytic virus composition of the present invention, the cytokine is selected from: GM-CSF, IL-2 and IL-12. In some embodiments, in the aforementioned recombinant oncolytic virus composition of the present invention, in terms of pfu, the mixing ratio of the first recombinant oncolytic virus to the second recombinant oncolytic virus is about 0.5:2-2:0.5, preferably 0.5:1-1:0.5, most preferably 1:1.

The endpoints and any values in the ranges disclosed herein are not limited to the precise ranges or values, and these ranges or values should be understood to include values close to these ranges or values. For numerical ranges, one or more new numerical ranges can be obtained by combining each of the endpoint values of each range, each of the endpoint values of each range and the individual point values, and each of the individual point values. These numerical ranges should be considered as specifically disclosed herein.

In the present invention, the gene encoding ICP34.5, the gene encoding ICP47, the gene encoding ICP6, the gene encoding TK, and the gene encoding UNG are all known to those skilled in the art, and can also be found by logging into relevant databases, for example, relevant nucleotide sequences can be found by logging in to the GenBank database. These are conventional technical means possessed by those skilled in the art, and will not be repeated in the present invention.

In the present invention, the type of herpes simplex virus is not particularly limited. It may be type I herpes simplex virus or type II herpes simplex virus, but is preferably type I herpes simplex virus. The source of herpes simplex virus is not particularly limited in the present invention, and it can be obtained by conventional commercial purchase, or it can be obtained by isolation in laboratory or clinically.

The recombinant oncolytic virus composition of the present invention can be mixed with a pharmaceutically acceptable carrier to prepare a pharmaceutical composition; it can also be packaged in a container, together with a package insert that describes the use and method of use of the recombinant oncolytic virus composition for the preparation of a kit or a product.

3. Exogenous Gene, Recombinant Herpes Simplex Virus

The present invention relates to an oncolytic virus composition, comprising: a first recombinant oncolytic virus, the first recombinant oncolytic virus comprising a first herpes simplex virus vector and a first exogenous gene; a second recombinant oncolytic virus, the second recombinant oncolytic virus comprising a second herpes simplex virus vector and a second exogenous gene. The first herpes simplex virus vector and the second herpes simplex virus vector are the same or different from each other, and the selected first exogenous gene is different from the selected second exogenous gene. The first herpes simplex virus vector and the second herpes simplex virus vector of the present invention carry exogenous genes, for example, the first herpes simplex virus vector carries the first exogenous gene, and the exogenous gene is a gene encoding any one selected from the following: cytokine, a monoclonal antibody having preventative and/or therapeutic effect on tumor, a tumor antigen, prodrug invertase, a tumor suppressor protein, antisense RNA or small RNA that blocks or down-regulates overexpressed proto-oncogene and a metabolic gene in tumor; the second herpes simplex virus vector carries the second exogenous gene, which encodes a gene any one selected from the group consisting of: cytokine, a monoclonal antibody having preventative and/or therapeutic effect on tumor, a tumor antigen, prodrug invertase, a tumor suppressor protein, antisense RNA or small RNA that blocks or down-regulates overexpressed proto-oncogene and a metabolic gene in tumor. The coding sequences of these exogenous genes optionally include part or all of 5' and/or 3' transcribed but untranslated flanking sequences naturally linked to or related to the translated coding sequences. Optionally, transcription control sequences usually related to transcription sequences, such as transcription termination signals, polyadenylation sites, and downstream enhancer elements may also be included.

By homologous recombination between the HSV strain and, for example, a plasmid vector carrying one or more exogenous genes adjacent to HSV sequence, the one or more exogenous genes can be inserted into the virus vector genome. Using conventional cloning techniques known to those skilled in the art (see, for example, Sambrook et al., 1989, Molecular Cloning-A laboratory manual; Cold Spring Harbor Press), one or more exogenous genes can be inserted into any position in the viral genome with the premise that the virus can still reproduce. Heterologous genes can be inserted at multiple sites within the viral genome.

4. Therapeutic Application

The oncolytic virus composition of the present invention can be used in a therapeutic method. Specifically, the oncolytic virus composition of the present invention can be used in the treatment of cancer, for example, by direct intratumoral injection. The oncolytic virus composition of the present invention can be used to treat any solid tumors in a mammal, preferably a human. For example, the virus of the present invention can be administered to subjects suffering from the following diseases: brain glioma, melanoma, liver cancer, lung cancer, colorectal cancer, head and neck tumors, breast cancer, renal cell carcinoma, ovarian cancer, prostate cancer, stomach cancer, lymphoma, pancreatic cancer, bladder cancer, breast cancer, endometrial cancer, lymphoma, sarcoma (such as soft tissue sarcoma and osteosarcoma).

5. Dosing Regimen

The oncolytic virus composition of the present invention can be administered by directly injecting the composition into the target tissue. When injecting, the subject is usually injected with a pharmaceutical composition consisting of the oncolytic virus composition and a pharmaceutically acceptable suitable carrier or diluent. The injection dosage can be 1 μl-500 μl, for example, 500 μl, 400 μl, 300 μl, 200 μl, 100 μl, 50 μl. However, according to the tumor and the inoculation site, larger volumes of 10 ml, 8 ml, 6 ml, 5 ml, 4 ml, 3 ml can also be used. Since those skilled in the art can easily determine the optimal administration route and dosage according to the specific situation, the administration route and dosage are merely illustrative. The dosage can be determined according to various parameters, especially according to the age, weight and a disorder of the patient to be treated, the severity of the disease or disorder, and the route of administration.

EXAMPLE

Preparation Example 1

This preparation example was used to prepare a recombinant oncolytic virus (GM-CSF gene, IL-2 gene)

The ICP34.5 gene and ICP47 gene of the wild-type HSV-1 virus (GenBank number of its gene sequence: NC_001806, the same below) were knocked out according to the method described in the patent application with application number 2004100064921 and number of announcement of grant of patent right CN1283803C, and into the position of the knocked out gene ICP34.5 in HSV-1 was inserted respectively with: (1) the gene encoding murine GM-CSF (5'-end to 3'-end including in turn: CMV promoter, GM-CSF gene (Gene ID: 12981, the same below), BGH-PolyA sequence); (2) the gene encoding murine IL-2 (5' end to 3' end including in turn: EF1 promoter, IL-2 gene (Gene ID: 16183, the same below), TKPolyA sequence); (3) the genes encoding the dual expression cassette of both murine GM-CSF and murine IL-2 (5' end to 3' end including in turn: CMV promoter, GM-CSF gene, BGHPolyA sequence, EF1 promoter, IL-2 gene, TKPolyA sequence). Abtained were the recombinant oncolytic virus A1-1 containing the gene encoding murine GM-CSF, the recombinant oncolytic virus A1-2 containing the gene encoding murine IL-2, and the recombinant oncolytic virus D1 containing the gene encoding the dual expression cassette of murine GM-CSF and murine IL-2.

Sequencing at Beijing Sunbiotech Company confirmed that GM-CSF and IL-2 genes were correctly inserted into the herpes simplex virus vector. The successfully constructed recombinant virus vector was propagated on host cells Vero at 37° C. and 5% $CO_2$, cell debris was removed after harvest, and the virus suspension obtained after purification by high-speed centrifugation was used in an experiment.

Preparation Example 2

This preparation example was used to prepare a recombinant oncolytic virus (GM-CSF gene, PD-1 monoclonal antibody gene)

The ICP34.5 gene and ICP47 gene of the wild-type HSV-1 virus (GenBank number of its gene sequence: NC_001806, the same below) were knocked out according to the method described in the patent application with the application number 2004100064921 and number of announcement of grant of patent right CN1283803C, and the gene encoding the murine PD-1 monoclonal antibody (J43, BioXCell, the same below) (5' end to 3'end including in turn: CMV promoter, PD-1 monoclonal antibody gene, BGH-PolyA sequence) was inserted into the position of the knocked out ICP34.5 gene in HSV-1 virus to obtain a recombinant oncolytic virus B1-2 containing the gene encoding murine PD-1 monoclonal antibody. On the basis of B1-2, the gene encoding murine GM-CSF (5' end to 3'end including in turn: EF1 promoter, GM-CSF gene, TK PolyA sequence) was inserted into the position of knocked out ICP47 gene to obtain the comparative recombinant oncolytic virus D2 comprising the gene encoding the dual expression cassette of murine GM-CSF and murine PD-1 monoclonal antibody.

Sequencing at Beijing Sunbiotech Company confirmed that GM-CSF and PD-1 monoclonal antibody genes were correctly inserted into the herpes simplex virus vector. The successfully constructed recombinant virus vector was propagated on Vero host cells at 37° C. and 5% $CO_2$, cell debris was removed after harvest, and the virus suspension obtained after purification by high-speed centrifugation was used in an experiment.

Preparation Example 3

This preparation example was used to prepare a recombinant oncolytic virus (IL-12 gene, GM-CSF gene)

The ICP34.5 gene and ICP47 gene of the wild-type HSV-1 virus (GenBank number of its gene sequence: NC_001806, the same below) were knocked out according to the method described in the patent application with application number 2004100064921 and number of announcement of grant of patent right CN1283803C, and into the position of knocked out ICP34.5 gene in HSV-1 virus was inserted respectively with: (1) the gene encoding murine IL-12 (5' end to 3' end, including in turn: EF1 promoter, IL-12 gene (Gene ID: 16159, 16160), TK PolyA sequence); (2) the gene encoding the dual expression cassette of both murine GM-CSF and murine IL-12 (5'-end to 3'-end including in turn: CMV promoter, GM-CSF gene, BGH PolyA sequence, EF1 promoter, IL-12 gene, TK PolyA sequence). Obtained were the recombinant oncolytic virus C1-1 containing the gene encoding murine IL-12, the comparative recombinant oncolytic virus D3 containing the gene encoding the dual expression cassette of murine GM-CSF and murine IL-12.

Sequencing at Beijing TsingKe Biological Technology Company confirmed that both IL-12 and GM-CSF genes were correctly inserted into the herpes simplex virus vector. The successfully constructed recombinant virus vector was propagated on Vero host cells at 37° C. and 5% $CO_2$, cell debris was removed after harvest, and the virus suspension obtained after purification by high-speed centrifugation was used in experiments.

Preparation Example 4

This preparation example is used to prepare a recombinant oncolytic virus (PD-1 monoclonal antibody gene, IL-2 gene and IL-12 gene)

Prepare B1-2 in the same way as in Preparation Example 2. On the basis of B1-2, the gene encoding murine IL-2 (5' end to 3' end including in turn: EF1 promoter, IL-2 gene, TK PolyA sequence) and the gene encoding murine IL-12 (5' end to 3' end including in turn: EF1 promoter, IL-12 gene, TK PolyA sequence) were inserted into the knocked out position of ICP47 gene respectively to obtain the recombinant oncolytic virus D4 containing the dual expression cassette of the PD-1 monoclonal antibody and murine IL-2, and the comparative recombinant oncolytic virus D5 containing the gene encoding the dual expression cassette of murine PD-1 monoclonal antibody and murine IL-12.

Sequencing at Beijing TsingKe Biological Technology Company confirmed that the PD-1 monoclonal antibody gene, IL-2 and IL-12 genes were correctly inserted into the herpes simplex virus vector. The successfully constructed recombinant virus vector was propagated on Vero host cells at 37° C. and 5% $CO_2$, cell debris was removed after harvest, and the virus suspension obtained after purification by high-speed centrifugation was used in an experiment.

Test Example 1

Cell Experiment

HepG2 cells and A549 cells were respectively seeded into six-well plates, and propagated and cultured at 37° C. and 5% $CO_2$. After adherence, the same amount of recombinant oncolytic virus (multiplicity of infection MOI=0.1) according to Table 1 below was added respectively to infect HepG2 cells and A549 cells. After culturing at 37° C. and 5% $CO_2$ for 48 hours, the concentrations of GM-CSF and IL-2 in the cell culture supernatant were determined by ELISA. The results are shown in Table 1.

TABLE 1

|  | HepG2 cell | | A549 cell | |
| --- | --- | --- | --- | --- |
|  | GM-CSF concentration(pg/mL) | IL-2 concentration(pg/mL) | GM-CSF concentration(pg/mL) | IL-2 concentration(pg/mL) |
| A1-1:A1-2 (1:1) | 1560 | 4875 | 1359 | 2110 |
| D1 | 646 | 1656 | 282 | 220 |
| HSV-mock | 0 | 0 | 0 | 0 |

HSV-mock is an oncolytic virus without exogenous gene insertion and with the ICP34.5 gene and ICP47 gene knockout

Test Example 2

Cell Experiment

Vero cells were seeded into a six-well plate, propagated and cultured at 37° C. and 5% $CO_2$. After adherence, the same amount of recombinant oncolytic virus (multiplicity of infection MOI=0.1) according to Table 2 below was added respectively to infect Vero cells. After culturing at 37° C. and 5% $CO_2$ for 48 hours, the concentrations of GM-CSF and PD-1 monoclonal antibody in the cell culture supernatant were determined by ELISA. The results are shown in Table 2.

TABLE 2

|  | Vero cell | |
| --- | --- | --- |
|  | GM-CSF concentration (ng/mL) | PD-1 concentration (ng/mL) |
| A1-1:B1-2 (1:1) | 4.0 | 9.1 |
| D2 | 2.3 | 4.7 |
| HSV-mock | 0 | 0 |

HSV-mock is an oncolytic virus without exogenous gene insertion and with ICP34.5 gene and ICP47 gene knockout.

Test Example 3

Animal Experiment

C57BL/6 mice were inoculated subcutaneously with murine melanoma B 16F10 cell line to construct animal models. Successful model mice were selected. 9 groups were set up with 5 mice in each group. Administration was performed according to the method in Table 3. The total pfu of virus administered was $10^6$ pfu. The relative tumor inhibition rate after 14 days administration was adopted as the judgement criterion.

Relative tumor inhibition rate TGI (%): TGI %=(1−T/C)× 100%. T/C % is the relative tumor proliferation rate, that is, the percentage of the relative tumor volume of the treatment group to the control group at a specific time point. T and C are the relative tumor volumes (RTV) of the treatment group and the control group at a specific time point, respectively. RTV=animal tumor volume after treatment/tumor volume in control group.

TABLE 3

|  |  | Relative tumor inhibition rate (%) |
|---|---|---|
| A1-1:B1-2 | 1:1 | 81 |
|  | 1:2 | 85 |
|  | 1:3 | 91 |
|  | 1:4 | 83 |
| D2 |  | 77 |
| Negative control (PBS) |  | — |
| HSV-mock |  | 45 |
| A1-1 group |  | 58 |
| B1-2 group |  | 67 |

HSV-mock is an oncolytic virus without exogenous gene insertion and with ICP34.5 gene and ICP47 gene knockout Test Example 4

Animal Experiment

Balb/c mice were inoculated subcutaneously with murine hepatocarcinoma H22 cell line to construct animal models. Successful model mice were selected. 8 groups were set up with 5 mice in each group. Administration was performed according to the method in Table 4. The total pfu of virus administered was $10^6$ pfu. The relative tumor inhibition rate was adopted as the judgement criterion.

The relative tumor inhibition rate was calculated with reference to Test Example 3.

TABLE 4

|  |  | Relative tumor inhibition rate (%) |
|---|---|---|
| A1-1:A1-2 | 1:0.5 | 81 |
|  | 1:1 | 85 |
|  | 1:2 | 72 |
| DI |  | 76 |
| Negative control (PBS) |  | — |
| HSV-mock |  | 41 |
| A1-1 group |  | 55 |
| A1-2 group |  | 59 |

It can be seen from Table 1 and Table 2 that in different cell lines, the mixture of virus vectors each carrying a single cytokine has higher exogenous gene expression than the virus vector carrying two cytokines.

It can be seen from Table 3 to Table 4 that the tumor killing effect of either HSV oncolytic viruses inserted with GM-CSF, IL-2 or PD-1 monoclonal antibody genes can be enhanced, and the effect produced by mixing two exogenous genes is more significant, indicating that there is a good synergy among oncolytic virus, GM-CSF and IL-2 genes, and among oncolytic virus, GM-CSF and PD-1 monoclonal antibody genes.

Test Example 5

Animal Experiment

C57BL/6 mice were inoculated subcutaneously with murine melanoma B16F10 cell line to construct animal models. Mice with a tumor volume of about 60 mm$^3$ were selected. 15 groups were set up with 10 mice in each group. Administration was performed according to the method in Table 5. The total pfu of virus administered was $10^6$ pfu. The relative tumor inhibition rate was adopted as the judgement criterion.

The relative tumor inhibition rate was calculated with reference to Test Example 3.

TABLE 5

|  |  | Relative tumor inhibition rate (%) |
|---|---|---|
| A1-2:B1-2 | 1:1 | 91 |
|  | 1:2 | 89 |
|  | 1:3 | 95 |
|  | 1:4 | 86 |
| C1-1:B1-2 | 1:1 | 83 |
|  | 1:2 | 92 |
|  | 1:3 | 96 |
|  | 1:4 | 86 |
| A1-1:A1-2 | 1:0.5 | 69 |
|  | 1:1 | 81 |
|  | 1:2 | 78 |
| A1-1:C1-1 | 1:0.5 | 72 |
|  | 1:1 | 89 |
|  | 1:2 | 82 |
| Negative control (PBS) |  | — |

Test Example 6

Animal Experiment

Balb/c mice were inoculated subcutaneously with murine hepatocarcinoma H22 cell line to construct animal models. Mice with a tumor volume of about 60 mm$^3$ were select. 16 groups were set up with 10 mice in each group. Administration was performed according to the method in Table 6. The total pfu of virus administered was $10^6$ pfu. The relative tumor inhibition rate was adopted as the judgement criterion.

The relative tumor inhibition rate was calculated with reference to Test Example 3.

|  |  | Relative tumor inhibition rate (%) |
|---|---|---|
| A1-1:B1-2 | 1:1 | 75 |
|  | 1:2 | 75 |
|  | 1:3 | 88 |
|  | 1:4 | 81 |
| A1-2:B1-2 | 1:1 | 89 |
|  | 1:2 | 90 |
|  | 1:3 | 94 |
|  | 1:4 | 81 |
| C1-1:B1-2 | 1:1 | 91 |
|  | 1:2 | 95 |
|  | 1:3 | 98 |
|  | 1:4 | 88 |
| A1-1:C1-1 | 1:0.5 | 83 |
|  | 1:1 | 91 |
|  | 1:2 | 88 |
| Negative control (PBS) |  | — |

Test Example 7

Animal Experiment

C57BL/6 mice were inoculated subcutaneously with murine lung cancer Lewis cell line to construct animal models. Mice with a tumor volume of about 60 mm³ were selected. 19 groups were set up, with 10 mice in each group. Administration was performed according to the method in Table 7. The total pfu of virus administered was 10⁶ pfu. The relative tumor inhibition rate was adopted as the judgement criterion.

The relative tumor inhibition rate was calculated with reference to Test Example 3.

|  |  | Relative tumor inhibition rate (%) |
|---|---|---|
| A1-1:B1-2 | 1:1 | 78 |
|  | 1:2 | 83 |
|  | 1:3 | 86 |
|  | 1:4 | 76 |
| A1-2:B1-2 | 1:1 | 77 |
|  | 1:2 | 81 |
|  | 1:3 | 88 |
|  | 1:4 | 67 |
| C1-1:B1-2 | 1:1 | 82 |
|  | 1:2 | 91 |
|  | 1:3 | 94 |
|  | 1:4 | 85 |
| A1-1:A1-2 | 1:0.5 | 61 |
|  | 1:1 | 76 |
|  | 1:2 | 72 |
| A1-1:C1-1 | 1:0.5 | 72 |
|  | 1:1 | 84 |
|  | 1:2 | 77 |
| Negative control (PBS) |  | — |

Test Example 8

Animal Experiment

Balb/c mice were inoculated subcutaneously with murine sarcoma S180 cell line to construct animal models. Mice with a tumor volume of about 60 mm³ were selected. 19 groups were set up with 10 mice in each group. Administration was performed according to the method in Table 8. The total pfu of virus administered was 10⁶ pfu. The relative tumor inhibition rate was adopted as the judgement criterion.

The relative tumor inhibition rate was calculated with reference to Test Example 3.

|  |  | Relative tumor inhibition rate (%) |
|---|---|---|
| A1-1:B1-2 | 1:1 | 64 |
|  | 1:2 | 77 |
|  | 1:3 | 80 |
|  | 1:4 | 71 |
| A1-2:B1-2 | 1:1 | 72 |
|  | 1:2 | 70 |
|  | 1:3 | 83 |
|  | 1:4 | 80 |
| C1-1:B1-2 | 1:1 | 79 |
|  | 1:2 | 87 |
|  | 1:3 | 87 |
|  | 1:4 | 73 |
| A1-1:A1-2 | 1:0.5 | 62 |
|  | 1:1 | 73 |
|  | 1:2 | 66 |
| A1-1:C1-1 | 1:0.5 | 74 |
|  | 1:1 | 80 |
|  | 1:2 | 78 |
| Negative control (PBS) |  | — |

It could be seen from the above test examples that when the ratios of A1-1:B1-2, A1-2:B1-2, and C1-1:B1-2 were 1:3, the tumor suppression effect is the best. When the ratio of A1-1:A1-2 and A1-1:C1-1 is 1:1, the tumor suppression effect is the best. In order to determine the best combination for tumor suppression, in the present patent, the following test examples were further implemented. The volume of the tumor to be treated was increased to about 200 mm³ for distinguishing the therapeutic effects of each combination.

Test Example 9

Animal Experiment

C57BL/6 mice were inoculated subcutaneously with murine melanoma B16F10 cell line to construct animal models. Mice with a tumor volume of about 200 mm³ were select. 15 groups were set up with 10 mice in each group. Administration was performed according to the method in Table 9. The total pfu of virus administered was 10⁶ pfu. The relative tumor inhibition rate was adopted as the judgement criterion.

The relative tumor inhibition rate was calculated with reference to Test Example 3.

|  |  | Relative tumor inhibition rate (%) |
|---|---|---|
| A1-1:B1-2 | 1:3 | 65 |
| D2 |  | 52 |
| A1-1 |  | 34 |
| B1-2 |  | 37 |
| A1-2:B1-2 | 1:3 | 80 |
| D4 |  | 59 |
| A1-2 |  | 38 |
| B1-2 |  | 37 |
| C1-1:B1-2 | 1:3 | 78 |
| D5 |  | 64 |
| C1-1 |  | 34 |
| B1-2 |  | 37 |
| A1-1:A1-2 | 1:1 | 62 |
| D1 |  | 52 |
| A1-1 |  | 34 |
| A1-2 |  | 38 |
| A1-1:C1-1 | 1:1 | 63 |
| D3 |  | 60 |
| A1-1 |  | 34 |
| C1-1 |  | 34 |
| Negative control (PBS) |  | — |

Test Example 10

Animal Experiment

Balb/c mice were inoculated subcutaneously with murine hepatocarcinoma H22 cell line to construct animal models. Mice with a tumor volume of about 200 mm³ were selected. 15 groups were set up with 10 mice in each group. Administration was performed according to the method in Table 10. The total pfu of virus administered was 10⁶ pfu. The relative tumor inhibition rate was adopted as the judgement criterion.

The relative tumor inhibition rate was calculated with reference to Test Example 3.

|  |  | Relative tumor inhibition rate (%) |
|---|---|---|
| A1-1:B1-2 | 1:3 | 62 |
| D2 |  | 60 |

-continued

|  |  | Relative tumor inhibition rate (%) |
|---|---|---|
| A1-1 |  | 28 |
| B1-2 |  | 30 |
| A1-2:B1-2 | 1:3 | 82 |
| D4 |  | 54 |
| A1-2 |  | 35 |
| B1-2 |  | 30 |
| C1-1:B1-2 | 1:3 | 87 |
| D5 |  | 71 |
| C1-1 |  | 24 |
| B1-2 |  | 30 |
| A1-1:A1-2 | 1:1 | 67 |
| D1 |  | 63 |
| A1-1 |  | 28 |
| A1-2 |  | 35 |
| A1-1:C1-1 | 1:1 | 74 |
| D3 |  | 69 |
| A1-1 |  | 28 |
| C1-1 |  | 24 |
| Negative control (PBS) |  | — |

Test Example 11

Animal Experiment

C57BL/6 mice were inoculated subcutaneously with murine lung cancer Lewis cell lines to construct animal models. Mice with a tumor volume of about 200 mm³ were selected. 15 groups were set up with 10 mice in each group. Administration was performed according to the method in Table 10. The total pfu of virus administered was 10⁶ pfu. The relative tumor inhibition rate was adopted as the judgement criterion.

The relative tumor inhibition rate was calculated with reference to Test Example 3.

|  |  | Relative tumor inhibition rate (%) |
|---|---|---|
| A1-1:B1-2 | 1:3 | 68 |
| D2 |  | 56 |
| A1-1 |  | 35 |
| B1-2 |  | 40 |
| A1-2:B1-2 | 1:3 | 77 |
| D4 |  | 58 |
| A1-2 |  | 31 |
| B1-2 |  | 40 |
| C1-1:B1-2 | 1:3 | 81 |
| D5 |  | 61 |
| C1-1 |  | 39 |
| B1-2 |  | 40 |
| A1-1:A1-2 | 1:1 | 64 |
| D1 |  | 58 |
| A1-1 |  | 35 |
| A1-2 |  | 31 |
| A1-1:C1-1 | 1:1 | 72 |
| D3 |  | 63 |
| A1-1 |  | 35 |
| C1-1 |  | 39 |
| Negative control (PBS) |  | — |

Test Example 12

Animal Experiment

Balb/c mice were inoculated subcutaneously with murine sarcoma S180 cell line to construct animal models. Mice with a tumor volume of about 200 mm³ were select. 15 groups were set up with 10 mice in each group. Administration was performed according to the method in Table 10. The total pfu of virus administered was 10⁶ pfu. The relative tumor inhibition rate was adopted as the judgement criterion.

The relative tumor inhibition rate was calculated with reference to Test Example 3.

|  |  | Relative tumor inhibition rate (%) |
|---|---|---|
| A1-1:B1-2 | 1:3 | 59 |
| D2 |  | 57 |
| A1-1 |  | 31 |
| B1-2 |  | 32 |
| A1-2:B1-2 | 1:3 | 70 |
| D4 |  | 51 |
| A1-2 |  | 29 |
| B1-2 |  | 32 |
| C1-1:B1-2 | 1:3 | 79 |
| D5 |  | 64 |
| C1-1 |  | 36 |
| B1-2 |  | 32 |
| A1-1:A1-2 | 1:1 | 57 |
| D1 |  | 48 |
| A1-1 |  | 31 |
| A1-2 |  | 29 |
| A1-1:C1-1 | 1:1 | 69 |
| D3 |  | 63 |
| A1-1 |  | 31 |
| C1-1 |  | 36 |
| Negative control (PBS) |  | — |

It could be seen from the above test examples that the combination groups with virus vectors has better tumor suppression effects than the groups with single viruses and the groups with dual cytokines, and the combination groups in which A1-2: B1-2 or C1-1: B1-2 is 1:3 has a better synergistic anti-tumor effect than other combination groups.

The preferred embodiments of the present invention are described in detail above, but the present invention is not limited thereto. Within the scope of the technical concept of the present invention, many simple modifications can be made to the technical solution of the present invention, including the combination of various technical features in any other suitable manners. These simple modifications and combinations should also be regarded as the content disclosed in the present invention, which is inside the protection scope of the present invention.

The invention claimed is:

1. A recombinant oncolytic virus composition, characterized in that the composition comprises:
   a first herpes simplex virus vector 1 (HSV-1) with a deletion of the genes encoding ICP34.5 and ICP47 and a first exogenous gene inserted in a position where the gene encoding ICP34.5 is deleted; wherein the first exogenous gene is selected from the group consisting of a gene encoding granulocyte-macrophage colony-stimulating factor (GM-CSF), a gene encoding Interleukin-2 (IL-2), and a gene encoding Interleukin-12 (IL-12); and
   a second herpes simplex virus vector 1 (HSV-1) with a deletion of the genes encoding ICP34.5 and ICP47 and a second exogenous gene inserted in a position where the gene encoding ICP34.5 is deleted; wherein the second exogenous gene is a gene encoding cytokine GM-CSF, or a gene encoding a programmed cell death protein 1 (PD-1) blocking monoclonal antibody,
   wherein, the first herpes simplex virus vector and the second herpes simplex virus vector are the same or different from each other, and the selected first exogenous gene is different from the selected second exogenous gene; and wherein, in terms of pfu, if the second exogenous gene is a gene encoding a cytokine, the mixing ratio of the first recombinant oncolytic virus to the second recombinant oncolytic virus is 0.5:1-1:0.5, if the second exogenous gene is a gene encoding a monoclonal antibody, the mixing ratio of the first recombinant oncolytic virus to the second recombinant oncolytic virus is 1:1-1:4.

2. A pharmaceutical composition, comprising the recombinant oncolytic virus composition of claim 1 and a pharmaceutically acceptable carrier.

3. A product or kit, comprising a vial containing the pharmaceutical composition of claim 2 and a package insert with information related to the use of the pharmaceutical composition.

4. A method for treating a tumor in a subject, comprising administering to the subject an effective amount of the recombinant oncolytic virus composition of claim 1.

5. The method according to claim 4, wherein the tumor is selected from at least one of the group consisting of brain glioma, melanoma, liver cancer, lung cancer, colorectal cancer, head and neck cancer, breast cancer, renal cell carcinoma, ovarian cancer, prostate cancer, gastric cancer, lymphoma, pancreatic cancer, bladder cancer, breast cancer, endometrial cancer, lymphoma, and sarcoma.

6. The method of claim 5, wherein the sarcoma is a soft tissue sarcoma or an osteosarcoma.

7. The recombinant oncolytic virus composition of claim 1, wherein the first exogenous gene is GM-CSF and the second exogenous gene is a PD-1 blocking monoclonal antibody.

8. The recombinant oncolytic virus composition of claim 1, wherein the first exogenous gene is IL-2 and the second exogenous gene is a PD-1 blocking monoclonal antibody.

9. The recombinant oncolytic virus composition of claim 1, wherein the first exogenous gene is IL-12 and the second exogenous gene is a PD-1 blocking monoclonal antibody.

10. The recombinant oncolytic virus composition of claim 1, wherein the first exogenous gene is IL-2 and the second exogenous gene is GM-CSF.

11. The recombinant oncolytic virus composition of claim 1, wherein the first exogenous gene is IL-12 and the second exogenous gene is GM-CSF.

* * * * *